United States Patent [19]

Marantz

[11] Patent Number: 5,532,168
[45] Date of Patent: Jul. 2, 1996

[54] TISSUE BIOPSY SPECIMEN STRAINER AND METHOD

[76] Inventor: Calvin Marantz, 6250 Westview Dr., Orange, Calif. 92669

[21] Appl. No.: 292,714

[22] Filed: Aug. 18, 1994

[51] Int. Cl.⁶ .............................. G01N 1/36; C12M 1/00
[52] U.S. Cl. .................... 436/176; 422/99; 422/101; 436/63; 436/183; 435/283.1; 435/284.1; 210/473; 210/474; 210/477; 210/482; 210/497.3; 248/94
[58] Field of Search ................ 210/473, 474, 477, 210/482, 497.3; 248/94; 422/99, 101; 436/63, 176, 177, 183; 435/287

[56] References Cited

U.S. PATENT DOCUMENTS

| | | | |
|---|---|---|---|
| 618,996 | 2/1899 | Riedel et al. | |
| 752,019 | 2/1904 | Adwen. | |
| 956,332 | 4/1910 | Fuller | 210/474 |
| 1,395,951 | 11/1921 | Ferdon. | |
| 1,413,442 | 4/1922 | Wilcox. | |
| 1,536,890 | 5/1925 | Lagemann | 248/94 X |
| 1,594,023 | 7/1926 | Sorenson. | |
| 1,950,378 | 3/1934 | Andrews | 248/94 X |
| 2,147,792 | 2/1939 | Knight | 210/509 |
| 2,533,815 | 12/1950 | Kelly. | |
| 2,663,430 | 12/1953 | Curtis | 210/497.3 X |
| 2,896,788 | 7/1959 | Hoffberger | 210/473 |
| 3,374,897 | 3/1968 | Martin. | |
| 3,861,975 | 1/1975 | Häuslein | 210/474 X |
| 4,176,588 | 12/1979 | Baron | 210/474 X |
| 4,220,541 | 9/1980 | Chang | 210/474 |
| 4,221,670 | 9/1980 | Ziemek | 210/474 |
| 4,321,139 | 3/1982 | Auclair | 422/101 X |
| 4,417,504 | 11/1983 | Yamamoto | 210/474 |
| 4,557,903 | 12/1985 | McCormick | 422/101 |
| 4,804,470 | 2/1989 | Calvillo et al. | 210/474 X |

OTHER PUBLICATIONS

M. J. Zbar et al. *Am. J. Clin. Path.* 1959, 32, 41–44.
G. L. Humason "Animal/Tissue Techniques" 3rd ed. W. H. Freeman Company: San Francisco, 1972, 12–13, 41–47, 262–264, and 454–455.
M. E. Boon et al, *Histopath*, 1986, 10, 303–309.
H. Nordgren et al, *AMPIS* 1989, 97, 136–142.

Primary Examiner—Robert J. Warden
Assistant Examiner—Arlen Soderquist
Attorney, Agent, or Firm—Price, Gess & Ubell

[57] ABSTRACT

An apparatus and method to simplify and accelerate the transfer of tissue biopsy samples from fixative to automatic tissue processing cassettes comprises a strainer device and a preformed filter. The strainer device is constructed from a perforated material such as stainless steel screen and is substantially conical in shape. The device is provided with a support ring attached to an upper edge of the cone; the ring is designed for positioning the device on a fixative collection container and for attaching a convenient handle. The tip of the cone is truncated, providing a planar collection surface. A preformed filter, also of conical shape with a flattened tip matching the collection surface, is inserted into the strainer device. Fixative, containing tissue biopsy samples, is poured into the device, and the samples rest on the flat bottom and sides near the bottom while the fixative flows through into the fixative collection container. The filter is removed from the strainer device, and folded with upper regions of the filter being brought into contact with the samples on the flat filter bottom. The filter is placed into an opened cassette and the cassette is closed. After infiltration with paraffin, the cassette is opened and the filter is torn along a perforated line, thus releasing the infiltrated tissue samples.

23 Claims, 5 Drawing Sheets

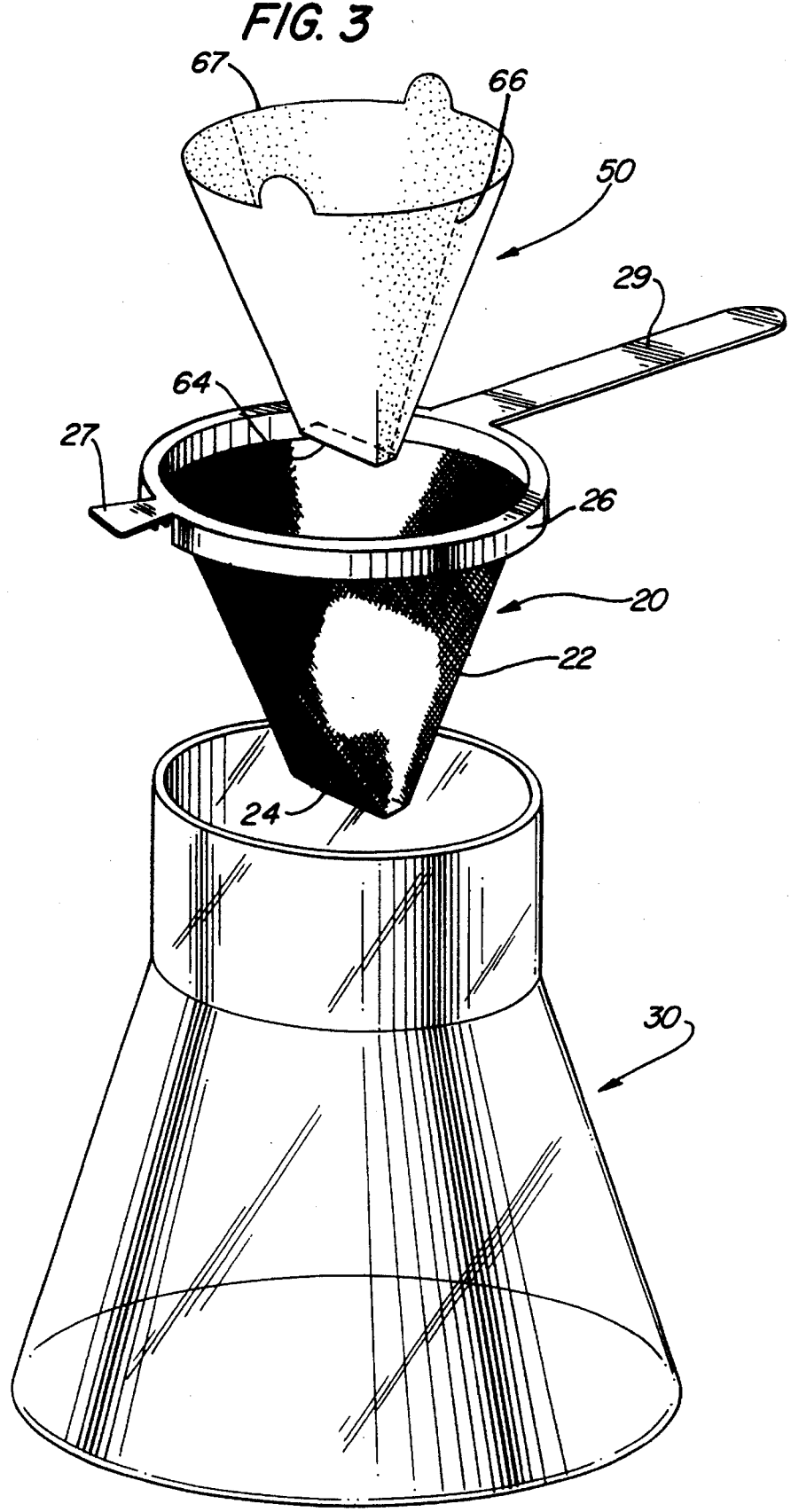

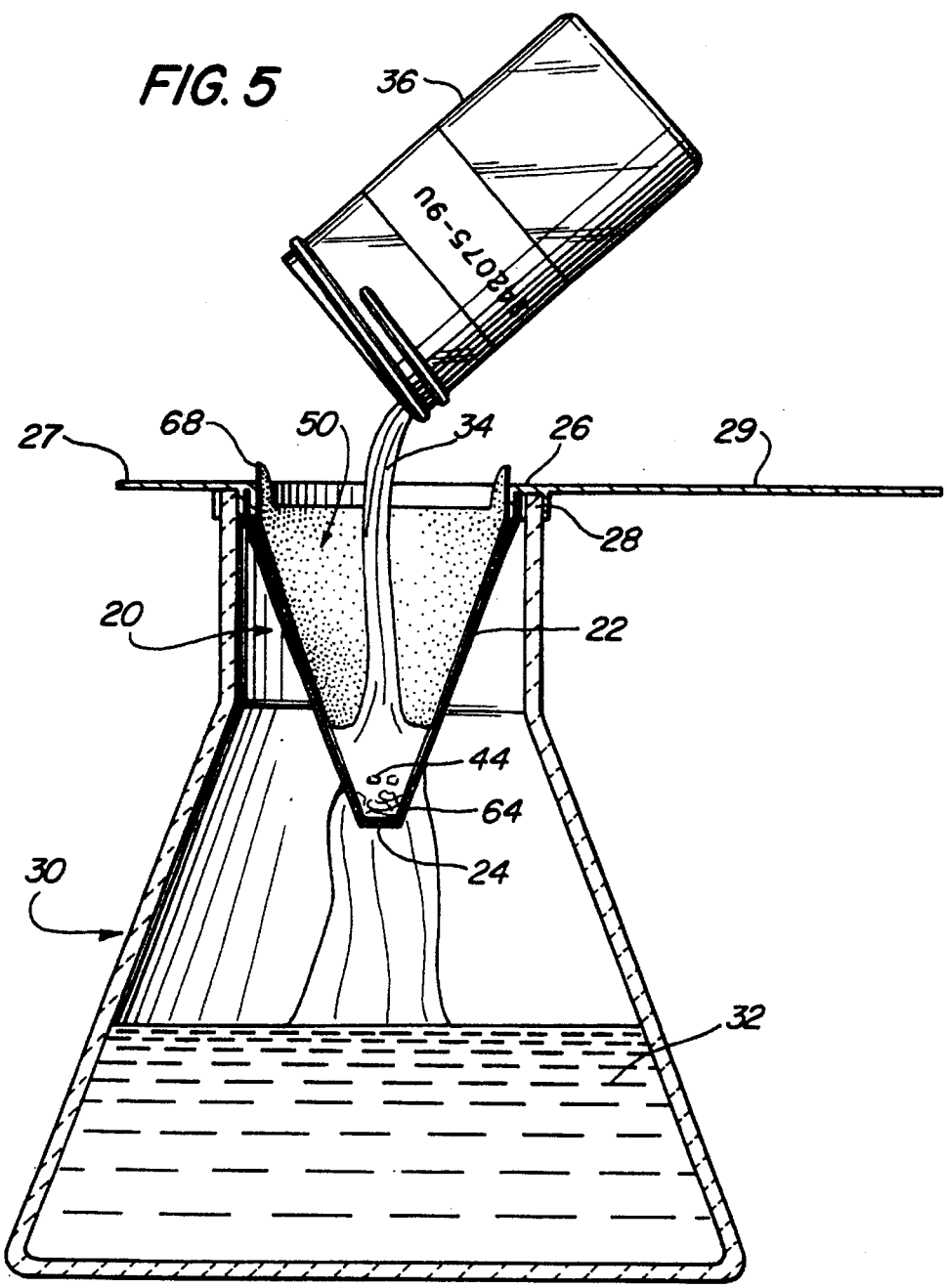
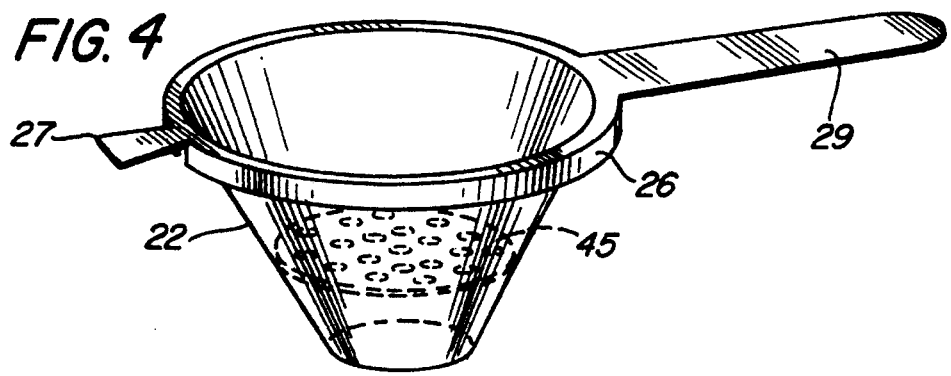

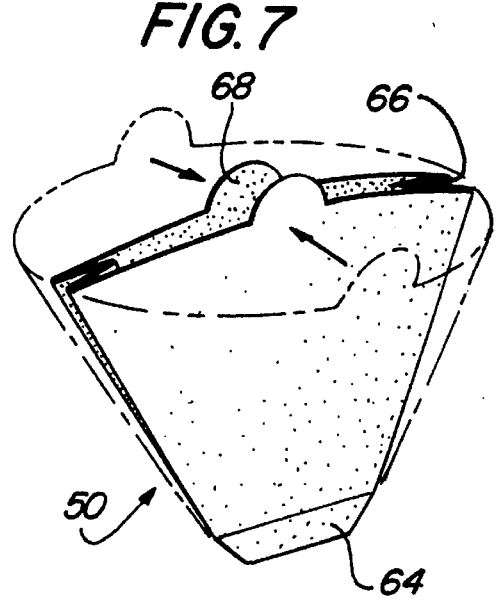
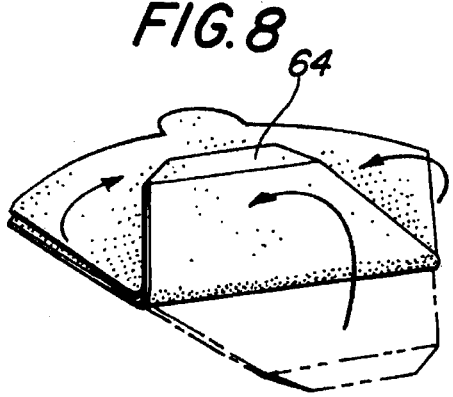
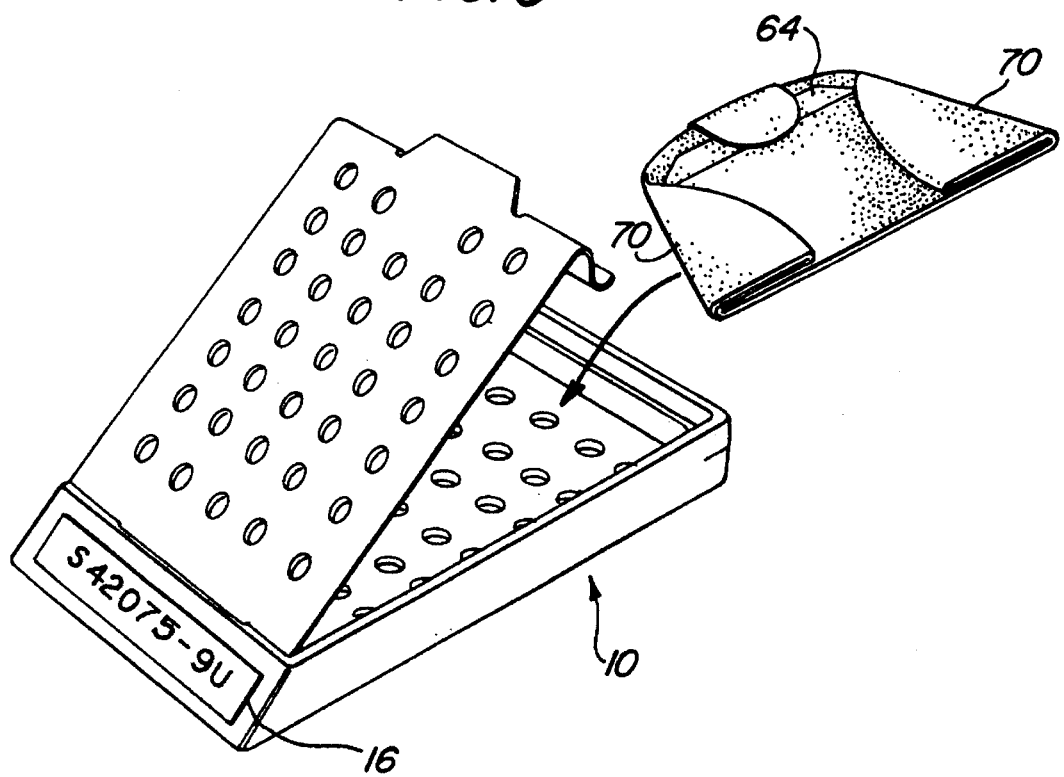

TISSUE BIOPSY SPECIMEN STRAINER AND METHOD

BACKGROUND OF THE INVENTION

1. Field of the Invention

The present invention relates generally to medical diagnosis of disease states from tissue samples and, more specifically, to a device and method for separating fragments of tissue biopsy samples from a fixative and capturing them for processing.

2. Description of Related Art

Many of us have noticed a strange-looking mole or felt a lump. "Is it cancer?" is often the first thought that comes to mind. Often a physician will take a look and tell us that there is nothing to worry about. At other times, the physician will have to take a biopsy or tissue sample from the patient at the physician's office, out patient department, or hospital. The tissue sample is then sent to a special pathology laboratory of a hospital or to a private pathology practice for diagnosis.

There the tissue is usually studied by a pathologist, a physician who is specially trained to recognize and interpret histological and cytological abnormalities. The pathologist can diagnose many disease states, as well as cancer. The pathologist provides a detailed written evaluation of tissue samples as an integral part of modern medicine. After the pathologist examines the sample and renders a gross description, the histology department processes and prepares sections of the sample, which are placed on slides for microscopic observation. Unfortunately, it is not always easy to properly prepare a tissue sample for proper evaluation. The suspicious tissue or growth may be tiny and located in an inaccessible area. Therefore, the tissues samples, which may be surgically cut, curetted, or scraped from the patient, many times consist of small fragments. These small samples are precious, since it may not be possible to procure a second sample, and since only one of many fragments may contain specific abnormal findings which allow the diagnosis to be made.

Furthermore, the process of preparing the tissue for microscopic examination is time-consuming and may result in losing or damaging the tissue sample. The samples are often obtained from a patient, measured and described by the pathologist, and placed directly in the fixative, usually 10% formalin. The fixation process preserves cellular detail, stabilizes the tissue, and makes the sample amenable to the later steps of processing. The tissue samples can be conveniently stored in the formalin fixative until processing is started by the histology department.

Preparation of microscope slides entails embedding the tissue in a hard matrix and preparing sections of the embedded tissue. Briefly, the process comprises removing the tissue samples from the fixative and dehydrating them by passing them through a graded series of mixtures of alcohols, xylene and paraffin. A dehydrated sample is first treated with xylene which is miscible both with alcohol and paraffin, allowing the alcohol to be replaced with xylene, and the xylene to be then replaced with paraffin. Thus, the tissue samples are infiltrated with a paraffin wax matrix material that will support the tissue when sections, usually 3–5 μm in thickness, are cut.

Considerable progress has been made in automating tissue processing for a busy histology laboratory. Various instruments are used to automatically dehydrate the samples and infiltrate them with paraffin. These instruments may be quite large and complex because they must contain a heated chamber to keep the paraffin molten. The first step is for the pathologist or a special assistant to remove the samples from the fixative and transfer them to a special processing cassette 10 (see FIG. 1). The processing cassette 10 comprises a base unit 12 and a lid 14. The lid 14 is removable so that samples can be easily placed into the cassette 10 (see FIG. 2). Both the base 12 and the lid 14 are perforated so that processing solutions may easily percolate through the cassette. Because formalin is toxic and allergenic, protective gloves are worn when the samples are transferred. One can easily crush or distort a particulate or fragile tissue sample. Unfortunately, the use of forceps may also crush the samples.

Once the tissue samples are in the cassette 10, they are automatically moved through the various solutions necessary to dehydrate and embed the tissue. The entire process usually takes between 4–12 hours. At the conclusion of the processing the paraffin-infiltrated samples are removed from the cassette 10 and cast into a block of paraffin for sectioning with a special microtome. The sections are placed on a glass microscope slide, xylene is used to remove the paraffin, and the sections are rehydrated and stained with special dyes to reveal cellular details. A thin glass coverslip is often placed over the stained sections, and the pathologist then microscopically examines the sections and arrives at a diagnosis.

Although the automatic processing instruments save considerable time and effort, they also introduce a number of problems. As already explained, the samples are often tiny and irreplaceable. Even if one laboriously removes all the tissue samples from the fixative and places them in the cassette, it is likely that some of the precious tissue biopsy samples will pass through the cassette perforations, or even through a space between the cassette base 12 and lid 14, and be lost during the infiltration process. In addition, pieces of tissue (called "floaters") may escape from one cassette and enter and mix with the samples in another cassette, thereby resulting in false diagnoses.

Workers have attempted to strain the tissue samples from the fixative, but the smallest samples often become stuck to the wire strainer and are damaged during removal. Likewise, attempts have been made to use filter material such as filter paper to capture the fragments, but removal of the samples from loose paper is cumbersome at best. The dilemma remains: the one tissue fragment that is lost during processing may be the sole sample that allows a proper diagnosis. Thus, the apparently simple problem of separating tissue samples from fixative may actually become a life-and-death matter.

OBJECTS AND SUMMARY OF THE INVENTION

It is an object of the present invention to provide an easily-used device and method for separating tissue biopsy samples from fixative;

It is another object of the present invention to provide a system for easily capturing the fixative for recycling or proper disposal;

It is still another object of the present invention to save time and labor by providing a rapid method of removing tissue biopsy samples from the fixative and placing them in an automatic processing cassette;

It is a further object of the present invention to provide a means to prevent loss of tissue samples during the infiltration process;

It is another object of the present invention to prevent the contamination of one sample with another during processing; and It is an additional object of the present invention to separate and retain the tissue samples without the use of force or manipulations that might distort the samples.

These and additional objects are met by the use of a system comprising a specialized strainer which supports a filter matrix. The filter matrix, sized to fit, is placed into the strainer, which is generally conical in form with a substantially flat lower end. The entire strainer is constructed of a fine nonreactive screen or other perforated material. The tissue samples settle onto the flat bottom portion while the fixative flows through into a special container. The filter matrix prevents the samples from sticking to the strainer mesh. After all the fixative has drained away, the entire filter matrix is lifted out. The filter is folded so that the filter will fit easily within an opened processing cassette. The cassette is closed and placed into a formalin bath, ready for later processing by an automatic tissue processing instrument. The filter matrix is sufficiently thin and porous that it does not interfere with infiltration, and yet prevents the tissue samples from falling through the cassette perforations. When the tissue is completely infiltrated with paraffin, the cassette is opened and perforations in the filter matrix allow one to tear open the matrix and retrieve the tissue samples.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 3 shows a strainer device of the present invention along with a wide bottomed collection container;

FIG. 4 shows an alternate embodiment of the strainer of the present invention with a collection surface formed by an inserted perforated disc;

FIG. 5 illustrates a cross-sectional view of the filter in place in the strainer of the present invention;

FIG. 7 shows the preformed filter of the present invention and initial steps of folding the preformed filter;

FIG. 8 shows completed folding of the filter of FIG. 7; and

FIG. 9 shows the folded filter being placed into the opened cassette.

DETAILED DESCRIPTION OF THE PREFERRED EMBODIMENTS

Figure 1:
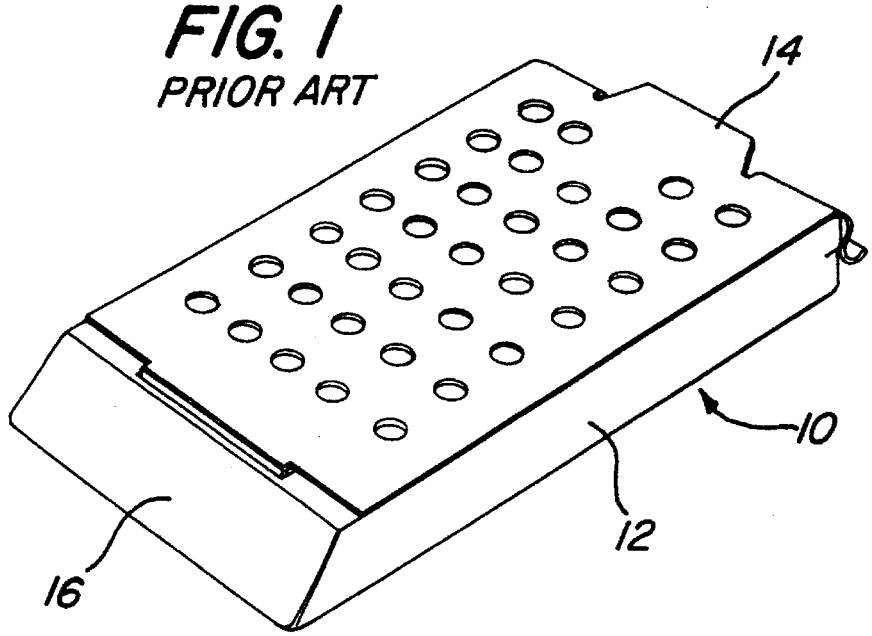
FIG. 1 shows a prior art cassette for an automatic tissue processing apparatus.
Figure 2:
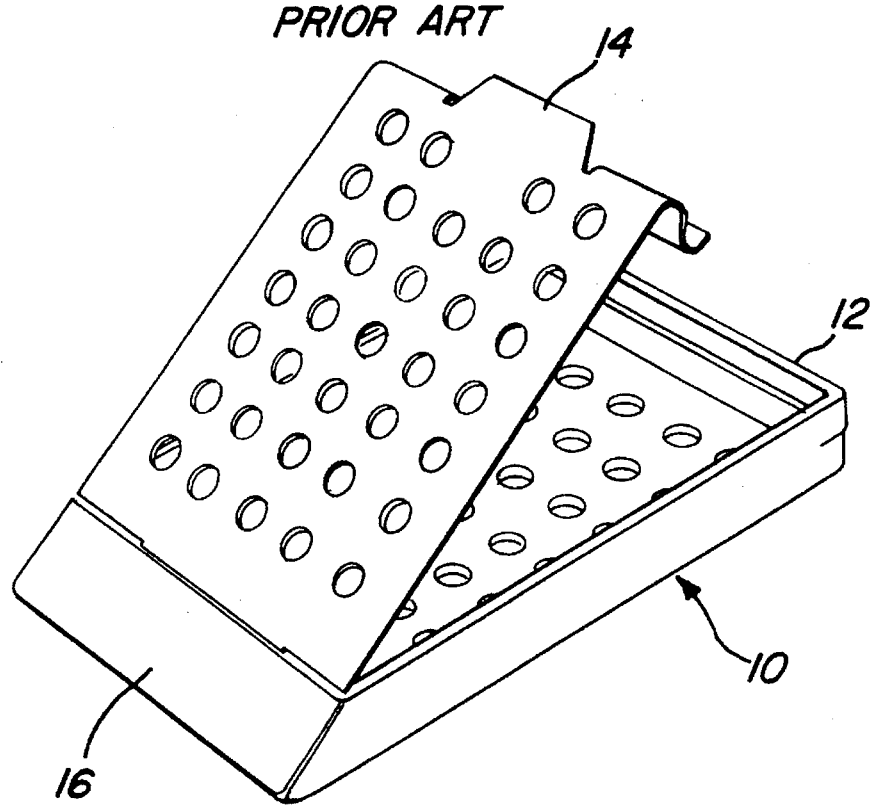
FIG. 2 shows the cassette of FIG. 1 in a partially open configuration.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a device and method for separation of tissue samples from fixative and for retention of the samples during further processing.

FIG. 3 shows a strainer 20 of the present invention along with a wide bottomed collection container 30 for catching the fixative. The strainer 20 has a hollow strainer body 22 that is funnel-like or cone-shaped. This body 22 is preferably constructed from a nonreactive material containing numerous perforations so that the fixative can readily drain away. Fine stainless steel screen is an ideal material, but perforated metals and plastics or other metallic or plastic screening may also be employed. Stainless steel screen has sufficient dimensional stability that supporting struts are normally not needed. Strainer bodies 22 of other materials may require an additional structure to stabilize the perforated material.

Preferably the strainer body 22 does not come to a point as in a true cone. Instead, the strainer body 22 is truncated and a planar collection surface 24 occupies the lower end of the cone. The purpose of the collection surface 24 is to provide a flat area for the tissue samples 44 to occupy for better exposure to solutions during processing. The collection surface 24 may be formed by flattening the screening material at the cone's tip as in FIG. 3. Alternatively, a substantially flat perforated disc 45 can be soldered or welded into the strainer body 22. The tip of the body 22 can be cut off (FIG. 4) or left intact. This method of producing the collection surface 24 is illustrated in FIG. 4, where a disc 45 of perforated material has been inserted into the conical strainer body 22. The disc 45 is of a larger diameter than a lower end of the cone. Therefore, the disc 45 rests inside the strainer body 22 in contact with an interior surface and suspended above the lower end of the cone. The disc 45 can be attached to the strainer body 22 by means of tabs (not shown) or can be welded or soldered to the strainer body 22. The lateral dimensions of the collection surface 24 are selected so that the area of the surface is smaller than the area of the cassette 10 of an automatic tissue processor that will be used on the tissue samples 44. The collection area 24 can be any convenient shape that fits into the cassette 10.

At its upper edge the conical strainer body 22 is attached to a support ring 26. The support ring 26 performs a number of functions. First, it provides a means of supporting the strainer 20 on a container 30. As mentioned above, the fixative is somewhat toxic and irritating. Therefore, it is important to provide a safe means of capturing the fixative as it is separated from the tissue samples 44. Further, there must be no chance that the strainer 20 will fall over and scatter the precious tissue samples 44. Therefore, the collection container 30 preferably has a wide-bottomed, tip-proof design as shown in FIGS. 3 and 5.

The support ring 26 is sized to fit a top of the fixative collection container 30. Generally, the support ring 26 has a groove 28 that fits the intended container. The ring may also be constructed with a wide enough rim to create a considerable overhang so that a variety of different-sized containers may be accommodated (not shown). The support ring 26 can also be formed with a lip or bear some other structure, such as a tab (not shown), that positively interacts with the container, or the ring 26 can bear a flange 27 that serves the same purpose as a wide rim so that a variety of containers larger in diameter than the ring 26 can be used. The support ring 26 can also be sized to fit readily-obtainable laboratory containers such as vials or beakers, although these containers are more prone to tipping over. Alternatively, the fixative container 30 can be a special size and shape that is produced exclusively for use with the strainer 20. A desirable container 30 would have an extra wide base, as shown in FIG. 3, to resist accidental tipping.

The support ring 26 also provides dimensional stability to the body 22 of the strainer. If the body 22 is constructed from stainless steel mesh or other screen-like material, the support ring 26, which is permanently attached to the screen, maintains the shape of the strainer body 22 without need for additional struts or other supporting structures. In addition, the support ring 26 provides an attachment place for a handle 29 so that the strainer 20 can be conveniently moved from container to container without any danger of splashing fixative around. The handle 29 is designed so that it is sufficiently light in weight that there is no danger of overbalancing the strainer 20 and/or tipping the fixative container 30. In actual practice the strainer 20 is frequently held above the container 30 during the pouring process as in FIG. 5. The strainer 20 is then placed onto the fixative collection container 30 to drain so that residual fixative 32 will be caught in the collection container 30.

The strainer 20 is ideal for separating the tissue samples 44 from the fixative. Larger samples are readily caught on the collection surface 24 and can then be removed for further processing. However, if small and fragile samples 44 are merely poured onto the collection surface 24, one will have a problem in removing the samples 44 from the perforated collection surface 24 without damaging the samples 44. To avoid this problem, preformed filters 50 are supplied for use with the strainer 20. Applicant has discovered that certain thin and porous materials such as lens paper such as Scientific Products catalog #P-1055 or "end papers" used in beauty salons during permanent wave processing can be included with the tissue and run through the entire tissue infiltration process without interfering with the process.

Figure 6:
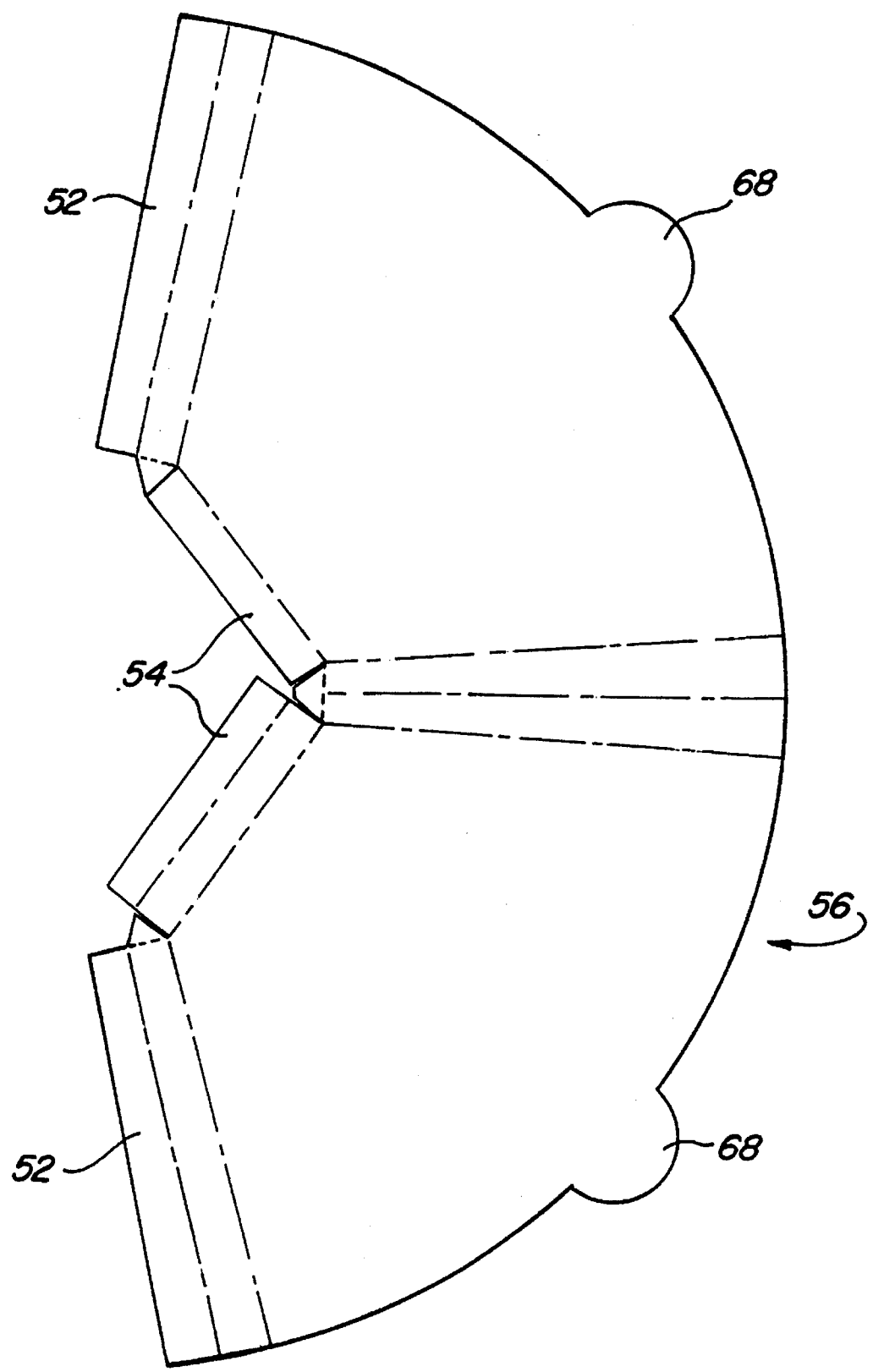
FIG. 6 illustrates one possible configuration for a filter blank cut from a permeable material and used to make a preformed filter of the present invention.

The preformed filters 50 are manufactured by cutting a filter blank 56 from the porous material; one configuration is as shown in FIG. 6. The cut blank 56 is folded and joined to form a substantially cone-shaped structure as shown in FIG. 3. Regions 54 of the filter blank are designed to overlap to create a flat bottom 64 to match the collection surface 24. The completed filter 50 is sealed along its side edges 52 and bottom edges 54 by a crimping process. At the same time, the filter 50 is perforated along a line 66 and back to the top edge 67 at a point about 180 degrees around the top edge 67. The perforated line 66 may be marked with an indelible ink during manufacture so that the line will be easy to see following processing. The completed filter 50 folds flat along the side edges (as in FIG. 7) so that it can be packaged in flat dispenser packs. For use the filter 50 is expanded and inserted into the strainer 20 and pressed down, as shown in FIG. 5, so that the flat bottom 64 of the filter 50 is contiguous with the collection surface 24 of the strainer 20. Alternatively, filters 50 can be manufactured without the built-in flat bottom 64 and the filters 50 can be pressed into the strainer 20 to deform a bottom edge of the filter 50, thereby creating a flat bottom surface.

The entire system 20, 50, comprising the strainer device and the preformed filter, is used as follows. First, the strainer 20 is placed on a suitable fixative container 30. Next, the preformed filter 50 is expanded and inserted into the strainer 20, taking care that the flat bottom 64 of the filter 50 coincides with the collection surface 24 of the strainer 20. An inserted filter 50 is illustrated in FIG. 5. Note tabs 68 that protrude above the support ring of the strainer device. For actual use the strainer-filter combination 20, 50 can be left on the container 50 or held above a suitable container or basin. The fixative 34 containing the tissue biopsies 44 is now poured into the filter-strainer combination. Water or, preferably, fixative is used to wash down the insides of a sample container 36 so that no samples are left behind. Care is taken to pour the fixative stream 34 directly onto the filter bottom 24. In this way the tissue biopsies 44 all end up on the collection surface 24. If any pieces adhere to slanted side regions of the filter 50, they can be washed down with a little extra fixative 34 or even with some clean water. If there is a large volume of biopsies 44, it may be preferable to allow some of the samples 44 to remain on the side regions in continuity with the samples 44 on the flat filter bottom 64 to present more surface area to processing chemicals during infiltration.

One then grasps the filter 50 by protruding tabs 68 using a forceps, hemostat, or other convenient tool. The entire filter 50 is then transferred to the opened cassette 10, which has previously been numbered. To fit the filter 50 into the cassette 10, the filter 50 is first flattened as shown in FIG. 7. The filter can then be folded so that the flat bottom 64 (containing the tissue samples) is brought closer to the tabs 68 as in FIG. 8. A final folding allows the filter 50 to be easily placed in the opened cassette 10 (FIG. 9). The flat bottom 64 of the filter 50 is sized to fit within the cassette 10. This way the samples 44 are completely enveloped by the filter material so that none of the sample 44 can fall through the perforation of the cassette 10, and so that there can be no possibility of part of a different sample getting mixed with the sample 44.

Although the cassette 10 is usually labelled on its outside bevel 16, a small label with the sample accession number can optionally be placed with the filter 50 before the cassette lid 14 is closed. After the cassette 10 is closed, it can be placed into the automatic processor for dehydration and infiltration. Alternatively, the entire cassette 10 can be stored in fixative to maintain the tissue samples 44 until they are processed. At the completion of the processing, the tissue samples 44 and the folded filter 50 will be completely infiltrated with paraffin. However, the tissue sample 44 can be easily recovered for embedding into paraffin blocks. One simply opens the cassette 10 and removes the paraffin-infiltrated filter 50 containing the tissue samples 44. If one grasps the folded filter at the tabs and pulls them in opposite directions, the filter 50 will pull open along the perforation line 66, thereby revealing the tissue samples 44. The samples 44 can then be removed from the filter surface and cast into a paraffin block for sectioning.

The present invention allows quick and simple recovery of tissue samples 44 from the fixative 34. Furthermore, the used fixative 32 is easily and safely collected for disposal or recycling. The strainer 20 alone can be used for large samples, while the filter-strainer system 20, 50 is best for small or delicate samples. The flat bottom 64 of the filter 50 provides a surface for the tissue samples 44 to spread out. The present invention simplifies transfer of the samples 44 to the processing cassette 10. In addition, the filter 50 protects the samples 44 in the cassette 10, preventing loss and avoiding cross-contamination. The perforations 66 make it easy to open the filters 50 to recover the samples 44 after they have been infiltrated with paraffin.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A system for separating tissue biopsy samples from a fixative for further tissue processing, the system consisting essentially of:

a strainer of substantially conical shape, the strainer comprising:

a strainer body being a hollow cone constructed of a perforated, inert material;

a support ring attached to an upper edge of the strainer body; and a substantially planar perforated collection disc of a diameter less than a maximum diameter of the strainer body, the disc inserted into the hollow cone parallel to an upper edge of the strainer body and attached to an inner surface of the strainer body; and a preformed filter constructed of a thin, permeable material, the filter having a truncated conical shape and sized to fit the strainer with a planar region of the filter coincident with the collection disc, the planar region sized to fit a tissue processing cassette when the filter is inserted therein.

2. The system of claim 1, wherein the preformed filter is further provided with perforations extending in a line from an upper edge of the filter to the planar region so that the filter can be readily opened at the end of tissue processing.

3. The system of claim 1, wherein the preformed filter is provided with tab-like extensions on an upper edge thereof so that the filter may be readily grasped to remove it from the strainer.

4. A method for separating tissue biopsy samples from a liquid fixative and for protecting the separated samples during transit through an automatic tissue processing apparatus, the method comprising the steps of:

providing a conically-shaped strainer system consisting essentially of a strainer body of an inert perforated material, the strainer body having a flat bottom with a preformed filter of thin, permeable material, the filter with a flat bottom region to fit the strainer body and inserted therein;

pouring a mixture of a liquid fixative and tissue biopsy samples into the strainer system so that the fixative passes through and the tissue samples are retained on the flat bottom;

removing the filter from the strainer body, folding a part of the filter over the tissue samples to envelope them, and placing the folded filter into an opened cassette of an automatic tissue processing apparatus, the flat bottom region of the filter sized to fit within the cassette;

closing the cassette;

placing the cassette into the automatic tissue processing apparatus and operating the process so that the filter and the tissue samples are infiltrated with paraffin; and removing the cassette from the apparatus, opening the cassette, and tearing open the filter to reveal the tissue samples, which are then ready to be mounted for microtoming.

5. The method of claim 4, wherein the preformed filter is further provided with perforations extending in a line from an upper edge of the filter to the flat bottom region of the filter so that the filter can be more readily opened when the filter and the tissue samples are infiltrated with paraffin.

6. The method of claim 4, wherein the preformed filter is provided with tab-like extensions on an upper edge thereof so that the filter may be readily grasped to facilitate removing it from the strainer.

7. A system for separating tissue biopsy samples from a fixative for further tissue processing, the system comprising:

a strainer of a substantially conical shape, the strainer consisting essentially of:

a strainer body being a hollow cone constructed of a perforated, inert material;

a support ring attached to an upper edge of the strainer body; and a perforated collection surface, substantially planar, and formed by flattening a lower end of the strainer body; and a preformed filter formed by folding a thin, permeable material and sealing a resulting juncture, the filter having a truncated conical shape and sized to fit the strainer with a planar region of the filter coincident with the collection surface, the planar region sized to fit within a tissue processing cassette when the filter is inserted therein.

8. The system of claim 7, wherein the preformed filter is further provided with perforations extending in a line from an upper edge of the filter to the planar region so that the filter can be readily opened at the end of tissue processing.

9. The system of claim 7, wherein the preformed filter is provided with tab-like extensions on an upper edge thereof so that the filter may be readily grasped to remove it from the strainer.

10. A system for separating tissue biopsy samples from a fixative for further tissue processing, the system comprising:

a strainer of substantially conical shape, the strainer consisting essentially of:

a strainer body being a hollow cone constructed of stainless steel screening;

a substantially planar collection surface of a diameter less than a maximum diameter of the strainer body and forming a truncated tip of the conical strainer;

an annular support ring attached to an upper edge of the strainer body, the ring having a circumferential groove to interact with an upper edge of a container; and a handle being an elongate member one end of which is attached to the ring; and a preformed filter formed by folding a thin, permeable material and sealing a resulting juncture, the filter having a truncated conical shape to fit the strainer with a planar region of the filter coincident with the collection surface, the planar region sized to fit within a tissue processing cassette.

11. The system of claim 10, wherein the collection surface is formed from a planar perforated disc, the disc inserted into the hollow cone parallel to the upper edge of the strainer body and attached to an inner surface of the strainer body.

12. The system of claim 10, wherein the collection surface is formed by flattening the screen of the strainer body during manufacture to create a planar tip region substantially parallel to the upper edge of the strainer body.

13. The system of claim 10, wherein the preformed filter is further provided with perforations that form a line from a starting point on an upper edge of the filter to the planar region and back to the upper edge at a point about 180 degrees from the starting point so that the filter can be more readily opened after paraffin infiltration.

14. The system of claim 10, wherein the preformed filter is provided with tab-like extensions on an upper edge thereof so that the filter may be readily grasped to facilitate removing it from the strainer.

15. A preformed filter for collecting tissue biopsy samples from a mixture of samples and a liquid, the filter comprising:

a truncated cone formed by folding a thin, permeable material and sealing a resulting juncture, the cone sized to fit a strainer;

a planar region at an apex of the cone, forming a collection surface; and a line of perforations from a starting point on an upper edge of the filter to the planar region and back to the upper edge at a point about 180 degrees from the starting point allowing the filter to be readily opened after paraffin infiltration.

16. The filter of claim 15, wherein the preformed filter is provided with tab-like extensions on the upper edge thereof to grasp the filter for removing the filter from the strainer.

17. A strainer system for separating tissue biopsy samples from a fixative for further tissue processing and for safely containing the separated fixative, the system comprising:

a strainer consisting essentially of:
   a strainer body being a hollow cone constructed of perforated, inert material;
   a collection surface being substantially planar and of a diameter less than a maximum diameter of the strainer body and forming a truncated tip of the conical strainer;
   an annular support ring attached to an upper edge of the strainer body; and
   a handle being an elongate member one end of which is attached to the ring; and
a tip resistant collection container for safely collecting the separated fixative and having means for interacting with the support ring of the strainer.

18. The strainer of claim 17, wherein the collection surface is formed from a planar perforated disc, the disc inserted into the hollow cone parallel to the upper edge of the strainer body and attached to an inner surface of the strainer body.

19. The strainer of claim 17, wherein the collection surface is formed by flattening the perforated material of the strainer body during manufacture to create a planar tip region substantially parallel to the upper edge of the strainer body.

20. A system for separating tissue biopsy samples from a fixative for further tissue processing, the system comprising:

a strainer of substantially conical shape, the strainer consisting essentially of:
   a strainer body being a hollow cone constructed of a perforated, inert material;
   a support ring attached to an upper edge of the strainer body; and
   a substantially planar perforated collection disc of a diameter less than a maximum diameter of the strainer body, the disc inserted into the hollow cone parallel to an upper edge of the strainer body and attached to an inner surface of the strainer body; and
a preformed filter constructed of a thin, permeable material, having a truncated hollow conical shape to fit the strainer with a planar region of the filter sized to fit within a tissue processing cassette and coincident with the collection disc, the filter having a line of perforations for facilitating opening the filter running from a point on an upper edge of the filter to the planar region.

21. A method for separating tissue biopsy samples from a liquid fixative and for protecting the separated samples during transit through an automatic tissue processing apparatus, the method comprising the steps of:

providing a strainer consisting essentially of a cone of an inert perforated material, with a flat tip, the strainer containing a preformed filter, sized to fit the strainer, of thin, permeable material with perforations extending in a line from an upper edge of the filter to a flat bottom region for facilitating opening the filter after tissue processing;

pouring a mixture of a liquid fixative and tissue biopsy samples into the strainer-filter combination so that the fixative passes through and the tissue samples are retained on the flat bottom;

removing the filter from the strainer, folding a part of the filter over the tissue samples to envelope them, and placing it into an opened cassette of an automatic tissue processing apparatus, the flat bottom of the filter fitting within the cassette;

closing the cassette;

placing the cassette into the automatic tissue processing apparatus and operating the process so that the filter and the tissue samples are infiltrated with paraffin; and removing the cassette from the apparatus, opening the cassette, and tearing open the filter along the perforations to reveal the tissue samples ready to be mounted for microtoming.

22. A system for separating tissue biopsy samples from a fixative for further tissue processing, the system comprising:

a strainer of a substantially conical shape, the strainer consisting essentially of:
   a strainer body being a hollow cone constructed of a perforated, inert material;
   a support ring attached to an upper edge of the strainer body; and
   a substantially planar perforated collection surface formed by flattening a lower end of the strainer body; and
a preformed filter formed by folding a thin, permeable material and sealing a resulting juncture, the filter having a truncated conical shape and sized to fit the strainer with a planar region of the filter coincident with the collection surface, the filter having perforations extending in a line from an upper edge of the filter to the planar region for facilitating opening the filter after tissue processing.

23. A system for separating tissue biopsy samples from a fixative for further tissue processing, the system comprising:

a strainer of substantially conical shape, the strainer consisting essentially of:
   a strainer body being a hollow cone constructed of stainless steel screening;
   a substantially planar collection surface forming a truncated tip of the conical strainer of a diameter less than a maximum diameter of the strainer body;
   an annular support ring attached to an upper edge of the strainer body, the ring having a circumferential groove to interact with an upper edge of a container; and
   a handle being an elongate member one end of which is attached to the ring; and
a preformed filter formed by folding a thin, permeable material and sealing a resulting juncture, the filter having a truncated conical shape to fit the strainer with a planar region of the filter coincident with the collection surface, the planar region sized to fit within a tissue processing cassette, the filter having a line of perforations from a point on an upper edge to the planar region facilitating opening the filter after tissue processing.

* * * * *